(12) United States Patent
Cave

(10) Patent No.: US 12,214,169 B2
(45) Date of Patent: *Feb. 4, 2025

(54) APPARATUS FOR RECORDING INFORMATION CONCERNING THE USE OF AN INJECTION DEVICE

(71) Applicant: Sanofi-Aventis Deutschland GMBH, Frankfurt am Main (DE)

(72) Inventor: George Cave, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/544,892

(22) Filed: Dec. 19, 2023

(65) Prior Publication Data

US 2024/0115809 A1 Apr. 11, 2024

Related U.S. Application Data

(60) Continuation of application No. 17/693,934, filed on Mar. 14, 2022, now Pat. No. 11,890,454, which is a
(Continued)

(30) Foreign Application Priority Data

Jan. 15, 2013 (EP) ..................................... 13151366

(51) Int. Cl.
*A61M 5/46* (2006.01)
*A61M 5/24* (2006.01)
(Continued)

(52) U.S. Cl.
CPC .......... *A61M 5/24* (2013.01); *A61M 5/31525* (2013.01); *A61M 5/31568* (2013.01);
(Continued)

(58) Field of Classification Search
CPC ....................................................... A61M 5/24
(Continued)

(56) References Cited

U.S. PATENT DOCUMENTS

| 533,575 A | 2/1895 | Wilkens |
| 4,395,259 A | 7/1983 | Prestele et al. |

(Continued)

FOREIGN PATENT DOCUMENTS

| CA | 2706408 | 7/2008 |
| CN | 1618075 | 5/2005 |

(Continued)

OTHER PUBLICATIONS

International Preliminary Report on Patentability in International Appln. No. PCT/EP2011/054283, dated May 2, 2012, 18 pages.
(Continued)

*Primary Examiner* — Reginald R Reyes
(74) *Attorney, Agent, or Firm* — Fish & Richardson P.C.

(57) ABSTRACT

Apparatus for recording information concerning the use of an injection device, the apparatus comprising: one or more sensors for providing information indicative of how the injection device is used; a processor configured to analyse said information detected by the one or more sensors to determine use information, said use information corresponding to how the injection device is used; and a memory for storing said use information in an image format such that said use information can be retrieved from the memory and displayed in an image.

20 Claims, 6 Drawing Sheets

Related U.S. Application Data division of application No. 17/340,927, filed on Jun. 7, 2021, now Pat. No. 11,285,265, which is a continuation of application No. 17/143,105, filed on Jan. 6, 2021, now Pat. No. 11,623,046, which is a continuation of application No. 14/760,428, filed as application No. PCT/EP2014/050464 on Jan. 13, 2014, now Pat. No. 10,888,662.

(51) Int. Cl.
  *A61M 5/315*  (2006.01)
  *G16H 20/17*  (2018.01)
  *G16H 30/20*  (2018.01)
  *A61M 5/31*  (2006.01)

(52) U.S. Cl.
  CPC ............. *G16H 20/17* (2018.01); *G16H 30/20* (2018.01); *A61M 2005/3125* (2013.01); *A61M 2005/3126* (2013.01); *A61M 2205/14* (2013.01); *A61M 2205/3306* (2013.01); *A61M 2205/3375* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/6081* (2013.01)

(58) Field of Classification Search
  USPC ........................................................ 604/207
  See application file for complete search history.

(56) References Cited

U.S. PATENT DOCUMENTS

| | | |
|---|---|---|
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,651,775 A | 7/1997 | Walker et al. |
| 5,674,204 A | 10/1997 | Chanoch |
| 5,688,251 A | 11/1997 | Chanoch |
| 5,792,117 A | 8/1998 | Brown |
| 5,921,966 A | 7/1999 | Bendek et al. |
| 5,928,201 A | 7/1999 | Poulsen et al. |
| 5,961,495 A | 10/1999 | Walters et al. |
| 6,004,297 A | 12/1999 | Steenfeldt-Jensen et al. |
| 6,113,578 A | 9/2000 | Brown |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,482,185 B1 | 11/2002 | Hartmann |
| 6,540,672 B1 | 4/2003 | Simonsen et al. |
| 6,899,698 B2 | 5/2005 | Sams |
| 6,936,032 B1 | 8/2005 | Bush et al. |
| 6,985,169 B1 | 1/2006 | Deng et al. |
| 7,138,806 B2 | 11/2006 | Gafner et al. |
| 7,241,278 B2 | 7/2007 | Moller |
| 7,595,726 B2 | 9/2009 | Nissels et al. |
| 7,749,186 B2 | 7/2010 | Kohlbrenner et al. |
| 7,801,058 B2 | 9/2010 | Wang |
| 7,933,780 B2 | 4/2011 | De La Huerga |
| 8,021,334 B2 | 9/2011 | Shekalim |
| 8,049,519 B2 | 11/2011 | Nielsen et al. |
| 8,128,604 B2 | 3/2012 | Yeandel et al. |
| 8,197,449 B2 | 6/2012 | Nielsen et al. |
| 8,221,356 B2 | 7/2012 | Enggaard et al. |
| 8,231,573 B2 | 7/2012 | Edwards et al. |
| 8,267,318 B2 | 9/2012 | Yoo |
| 8,469,922 B2 | 6/2013 | Langley et al. |
| 8,529,520 B2 | 9/2013 | Daniel |
| 8,556,847 B2 | 10/2013 | Kohlbrenner et al. |
| 8,556,865 B2 | 10/2013 | Krulevitch et al. |
| 8,556,866 B2 | 10/2013 | Krulevitch et al. |
| 8,556,867 B2 | 10/2013 | Krulevitch et al. |
| 8,560,271 B2 | 10/2013 | Koehler et al. |
| 8,568,361 B2 | 10/2013 | Yodfat et al. |
| 8,632,509 B2 | 1/2014 | Moller et al. |
| 8,743,662 B2 | 6/2014 | Sjolund et al. |
| 8,771,238 B2 | 7/2014 | Nielsen et al. |
| 8,817,258 B2 | 8/2014 | Whalley et al. |
| 8,920,724 B2 | 12/2014 | Nagai et al. |
| 8,926,553 B2 | 1/2015 | Langley et al. |
| 9,125,991 B2 | 9/2015 | Schabbach et al. |
| 9,152,829 B2 | 10/2015 | Day et al. |
| 9,186,465 B2 | 11/2015 | Jorgensen et al. |
| 9,192,726 B2 | 11/2015 | Butler et al. |
| 9,250,111 B2 | 2/2016 | Whalley et al. |
| 9,435,666 B2 | 9/2016 | Richter |
| 9,522,238 B2 | 12/2016 | Nielsen et al. |
| 9,526,842 B2 | 12/2016 | Oh et al. |
| 9,542,826 B2 | 1/2017 | Edwards et al. |
| 9,623,188 B2 | 4/2017 | Nielsen et al. |
| 9,638,564 B2 | 5/2017 | Whalley et al. |
| 9,642,968 B2 | 5/2017 | Whalley et al. |
| 9,734,302 B2 | 8/2017 | Nielson et al. |
| 9,764,095 B2 | 9/2017 | Draper |
| 9,836,948 B2 | 12/2017 | Edwards et al. |
| 10,105,489 B2 | 10/2018 | Edwards et al. |
| 10,117,999 B2 | 11/2018 | Andersen |
| 10,190,901 B2 | 1/2019 | Whalley et al. |
| 10,391,235 B2 | 8/2019 | Schabbach et al. |
| 10,684,156 B2 | 6/2020 | Whalley et al. |
| 11,062,799 B2 | 7/2021 | Schabbach et al. |
| 2001/0056258 A1 | 12/2001 | Evans |
| 2002/0052578 A1 | 5/2002 | Moller |
| 2002/0120235 A1 | 8/2002 | Enggaard |
| 2003/0050609 A1 | 3/2003 | Sams |
| 2003/0098022 A1 | 5/2003 | Nakao et al. |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0111745 A1 | 5/2005 | Kato |
| 2005/0113765 A1 | 5/2005 | Veasey et al. |
| 2005/0119786 A1 | 6/2005 | Kadaba |
| 2005/0275623 A1 | 12/2005 | Chadha |
| 2006/0153693 A1 | 7/2006 | Fiechter et al. |
| 2006/0178578 A1 | 8/2006 | Tribble et al. |
| 2007/0003113 A1 | 1/2007 | Goldberg |
| 2007/0033074 A1 | 2/2007 | Nitzan et al. |
| 2007/0142777 A1 | 6/2007 | Klein |
| 2007/0164992 A1 | 7/2007 | Liu et al. |
| 2007/0210157 A1 | 9/2007 | Miller |
| 2007/0239482 A1 | 10/2007 | Finn et al. |
| 2008/0004978 A1 | 1/2008 | Rothschild |
| 2008/0140444 A1 | 6/2008 | Karkanias et al. |
| 2008/0188813 A1 | 8/2008 | Miller et al. |
| 2008/0300920 A1 | 12/2008 | Brown et al. |
| 2009/0030366 A1 | 1/2009 | Hochman |
| 2009/0069742 A1 | 3/2009 | Larsen |
| 2009/0200185 A1 | 8/2009 | Follman et al. |
| 2009/0275916 A1 | 11/2009 | Harms et al. |
| 2009/0299279 A1 | 12/2009 | Richter |
| 2009/0314292 A1 | 12/2009 | Overfield |
| 2010/0127828 A1 | 5/2010 | Connolly et al. |
| 2010/0213255 A1 | 8/2010 | Yoo |
| 2011/0074830 A1 | 3/2011 | Rapp et al. |
| 2011/0124996 A1 | 5/2011 | Reinke et al. |
| 2011/0213621 A1 | 9/2011 | Dicks et al. |
| 2011/0282173 A1 | 11/2011 | Fonduca et al. |
| 2011/0313395 A1 | 12/2011 | Krulevitch et al. |
| 2011/0319729 A1 | 12/2011 | Donnay et al. |
| 2011/0320130 A1 | 12/2011 | Valdes et al. |
| 2012/0022458 A1 | 1/2012 | Oh et al. |
| 2012/0039809 A1 | 2/2012 | Levinson et al. |
| 2012/0072236 A1 | 3/2012 | Atkin |

(56) References Cited

U.S. PATENT DOCUMENTS

| | | | |
|---|---|---|---|
| 2012/0330555 | A1 | 12/2012 | Shaanan et al. |
| 2013/0072897 | A1 | 3/2013 | Day et al. |
| 2013/0195326 | A1* | 8/2013 | Bear .................. A61J 7/0084 |
| | | | 382/128 |
| 2013/0197445 | A1 | 8/2013 | Schabbach et al. |
| 2015/0306304 | A1 | 10/2015 | Schabbach et al. |
| 2015/0379900 | A1 | 12/2015 | Samosky et al. |
| 2016/0198243 | A1 | 7/2016 | Carnevale |
| 2017/0182258 | A1 | 6/2017 | Michael |
| 2018/0028759 | A1* | 2/2018 | Riedel ............... A61M 5/31566 |
| 2018/0085532 | A1 | 3/2018 | Desborough et al. |
| 2018/0099084 | A1 | 4/2018 | Schabbach et al. |
| 2018/0280624 | A1 | 10/2018 | Bitton et al. |
| 2018/0304028 | A1* | 10/2018 | Riedel ................. A61M 5/3202 |
| 2018/0369490 | A1 | 12/2018 | Rehbein et al. |
| 2019/0010604 | A1 | 1/2019 | Boyd et al. |
| 2019/0019306 | A1 | 1/2019 | Umanskiy et al. |
| 2019/0160229 | A1 | 5/2019 | Alagia et al. |
| 2021/0327561 | A1 | 10/2021 | Schabbach et al. |
| 2023/0021171 | A1 | 1/2023 | Schabbach et al. |

FOREIGN PATENT DOCUMENTS

| | | |
|---|---|---|
| CN | 101405738 | 4/2009 |
| CN | 101848742 | 9/2010 |
| EP | 0937471 | 8/1999 |
| EP | 0937476 | 8/1999 |
| EP | 1502514 | 2/2005 |
| EP | 1502614 | 2/2005 |
| JP | S61-116387 | 6/1986 |
| JP | H11-267207 | 10/1999 |
| JP | 2001-017542 | 1/2001 |
| JP | 2006-521183 | 9/2006 |
| JP | 2007-510469 | 4/2007 |
| JP | 2008-109292 | 5/2008 |
| JP | 2008-537491 | 9/2008 |
| JP | 2009-530002 | 8/2009 |
| JP | 2010-505475 | 2/2010 |
| JP | 2010-534552 | 11/2010 |
| JP | 2011-510749 | 4/2011 |
| KR | 10-2003-0014387 | 2/2003 |
| WO | WO 1999/038554 | 8/1999 |
| WO | WO 2001/010484 | 2/2001 |
| WO | WO 2003/063932 | 8/2003 |
| WO | WO 2004/087241 | 10/2004 |
| WO | WO 2005/046559 | 5/2005 |
| WO | WO 2006/083933 | 8/2006 |
| WO | WO 2007/107564 | 9/2007 |
| WO | WO 2009/018120 | 2/2009 |
| WO | WO 2009/024562 | 2/2009 |
| WO | WO 2009/097441 | 8/2009 |
| WO | WO 2010/003569 | 1/2010 |
| WO | WO 2010/128493 | 11/2010 |
| WO | WO 2011/089205 | 7/2011 |
| WO | WO 2011/117212 | 9/2011 |
| WO | WO 2014/011488 | 1/2014 |
| WO | WO 2014/111337 | 7/2014 |
| WO | WO 2021/034902 | 2/2021 |

OTHER PUBLICATIONS

International Preliminary Report on Patentability in International Appln. No. PCT/EP2014/050464, mailed on Jul. 30, 2015, 10 pages.
International Search Report and Written Opinion for International Appln. No. PCT/EP2014/050464, mailed on May 12, 2014, 15 pages.
International Search Report and Written Opinion in International Appln. No. PCT/EP2011/054283, mailed on Jul. 27, 2011, 18 pages.

* cited by examiner

```
BGM reading: 6.7mmol/L

Dose size: 40 units

Dose taken: 14:07, Wednesday 16th
November 2011

Image created 14:08, 16/11/2011
DoseSize0482.jpg
```

APPARATUS FOR RECORDING INFORMATION CONCERNING THE USE OF AN INJECTION DEVICE

CROSS REFERENCE TO RELATED APPLICATIONS

The present application is a continuation of U.S. patent application Ser. No. 17/693,934, filed Mar. 14, 2022, which is a divisional of U.S. patent application Ser. No. 17/340,927, filed Jun. 7, 2021, now U.S. Pat. No. 11,285,265, which is a continuation of U.S. patent application Ser. No. 17/143,105, filed Jan. 6, 2021, now U.S. Pat. No. 11,623,046, which is a continuation of U.S. patent application Ser. No. 14/760,428, filed Jul. 10, 2015, now U.S. Pat. No. 10,888,662, which is a U.S. National Phase Application pursuant to 35 U.S.C. § 371 of International Application No. PCT/EP2014/050464, filed Jan. 13, 2014, which claims priority to European Patent Application No. 13151366.5, filed Jan. 15, 2013. The entire disclosure contents of these applications are herewith incorporated by reference into the present application.

TECHNICAL FIELD

The present invention relates to an apparatus for recording information concerning the use of an injection device and relates particularly, but not exclusively, to an apparatus for recording information concerning the use of an injection device which is used to inject medicament such as insulin.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses which are administered. Supplemental devices may be used to record information about the various times at which insulin is administered and the quantity of insulin which is administered at each such time.

Some supplemental devices are not capable of displaying information about previously administered doses (or at least do not display all of the information they record). Dose history information may instead only be accessed using proprietary software on a computer which a person may not have access to at all times. The situation could therefore arise that a person cannot administer future doses on the basis of information concerning previously administered doses. In particular if a user were to forget how much insulin has been previously administered, and when the last injection took place, they will be required to guess the appropriate time of their next insulin dose and the quantity of insulin to be injected which is highly undesirable.

Aspects of the present invention have been conceived with the forgoing in mind.

SUMMARY

According to an aspect of the present invention there is provided apparatus for recording information concerning the use of an injection device, the apparatus comprising: one or more sensors for providing information indicative of how the injection device is used; a processor configured to analyse said information detected by the one or more sensors to determine use information, said use information corresponding to how the injection device is used; and a memory for storing said use information in an image format such that said use information can be retrieved from the memory and displayed in an image.

Advantageously, this improves the ease with which use information can be accessed since it is more likely that a device capable of displaying images will be accessible at a given time than a computer which has stored thereon proprietary software for both analysing and displaying data which concerns the use of an injection device.

The apparatus may be a supplemental device provided with a part for coupling the supplemental device to said injection device and the one or more sensors may be for detecting information displayed or generated by the injection device.

Advantageously, this enables the apparatus to be used in conjunction with an existing injection device.

The apparatus may be an integral part of said injection device.

Advantageously, this provides an injection device with enhanced functionality.

The memory may be configured to store said use information in a lossy image format. The memory may be configured to store said use information in raster format, vector format, compound format or stereo format. The memory may be configured to store said use information in .JPEG format.

The apparatus may further comprise a transmitter for wirelessly transmitting said use information to a remote device.

The memory may comprise a storage device that is removable from said apparatus.

The apparatus may further comprise an interface for receiving the storage device.

The memory may comprise another storage device that is not removable from said apparatus.

The processor may be configured to copy information from one storage device to another of said storage devices.

The apparatus may further comprise one or more user interface features that may be manipulated to cause the processor to copy information from one said storage device to another of said storage devices.

The storage device which is removable from said apparatus may be configured such that use information stored thereon is capable of being read by at least one of a digital camera, a computer, a mobile phone, a TV and an electronic photo frame.

The storage device that is removable from said apparatus may comprise an SD card, an XD card or a USB memory stick.

Said use information may relate to an amount of dose ejected from the injection device, the time when a dose was ejected from the injection device and/or a BGM reading.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
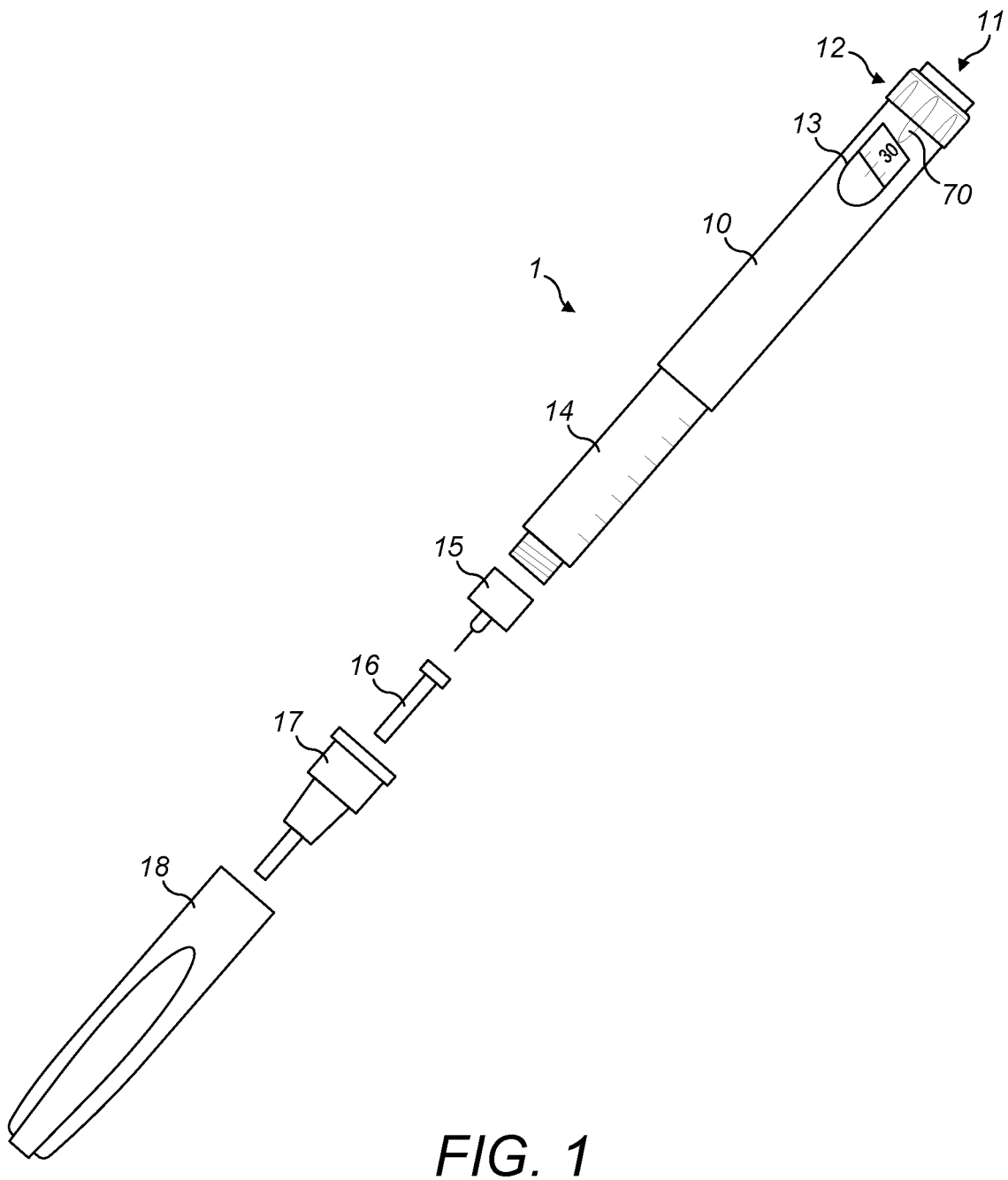
FIG. 1 is an exploded view of a prior art injection device 1.
Figure 2:
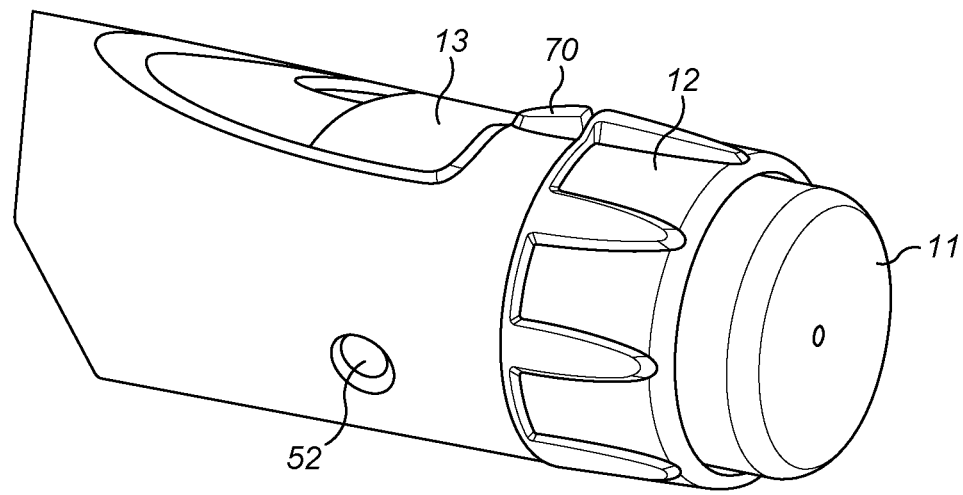
FIG. 2 is a perspective view of an end part of the device in FIG. 1.

FIG. 1 is an exploded view of an injection device 1, which may for instance represent Sanofi's Solostar (R) insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may be 30 IUs, as shown in FIG. 1. It should be noted that the selected dose may equally well be displayed differently, for instance by means of an electronic display.

Turning the dosage knob 12 causes a mechanical click sound to provide acoustical feedback to a user. The numbers displayed in dosage window 13 are printed on a sleeve that is contained in housing 10 and mechanically interacts with a piston within the insulin container 14. When needle 15 is stuck into a skin portion of a patient, and then injection button 11 is pushed, the insulin dose displayed in display window 13 is ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called prime shot to remove air from insulin container 14 and needle 15. This may be achieved by selecting two units of insulin and pressing injection button 11 while holding injection device 1 with the needle 15 pointing upwards.

For simplicity of presentation, in the following, it will be exemplarily assumed that the ejected doses substantially correspond to the injected doses, so that, for instance when making a proposal for a dose to be injected next, this dose equals the dose that has to be ejected by the injection device. Nevertheless, differences (e.g. losses) between the ejected doses and the injected doses may of course be taken into account.

Figure 3:
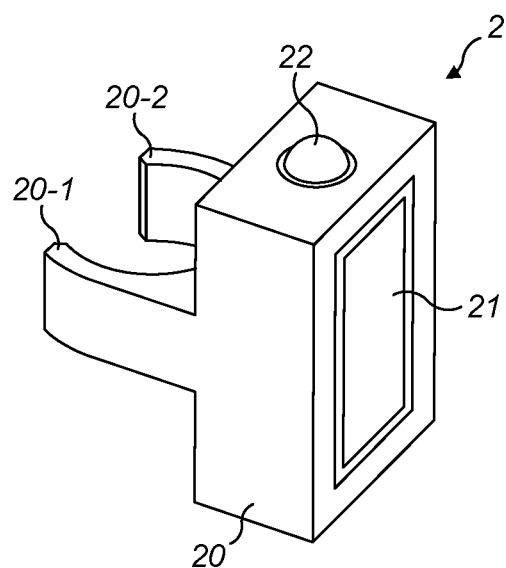
FIG. 3 is a schematic illustration of a supplemental device 2.

FIG. 3 is a schematic illustration of a supplemental device 2 which may be releasably attached to an injection device such as the one depicted in FIG. 1 for instance. It is envisaged however that the supplemental device 2 may be coupled to and used in conjunction with other types of injection devices of other types, and for administering different medicaments.

The supplemental device 2 comprises a housing 20 which is provided with a mating unit 20-1, 20-2 for embracing the housing 10 of an injection device. In particular the mating unit 20-1, 20-2 may be configured to snap-fit onto the housing 10 of an injection device 1 in such a way that the device 2 can be subsequently removed therefrom. The mating unit need not however be of the snap-fit variety and other arrangements may alternatively be suitable for coupling the supplemental device 2 to an injection device 1 such as a strap.

Figure 6:
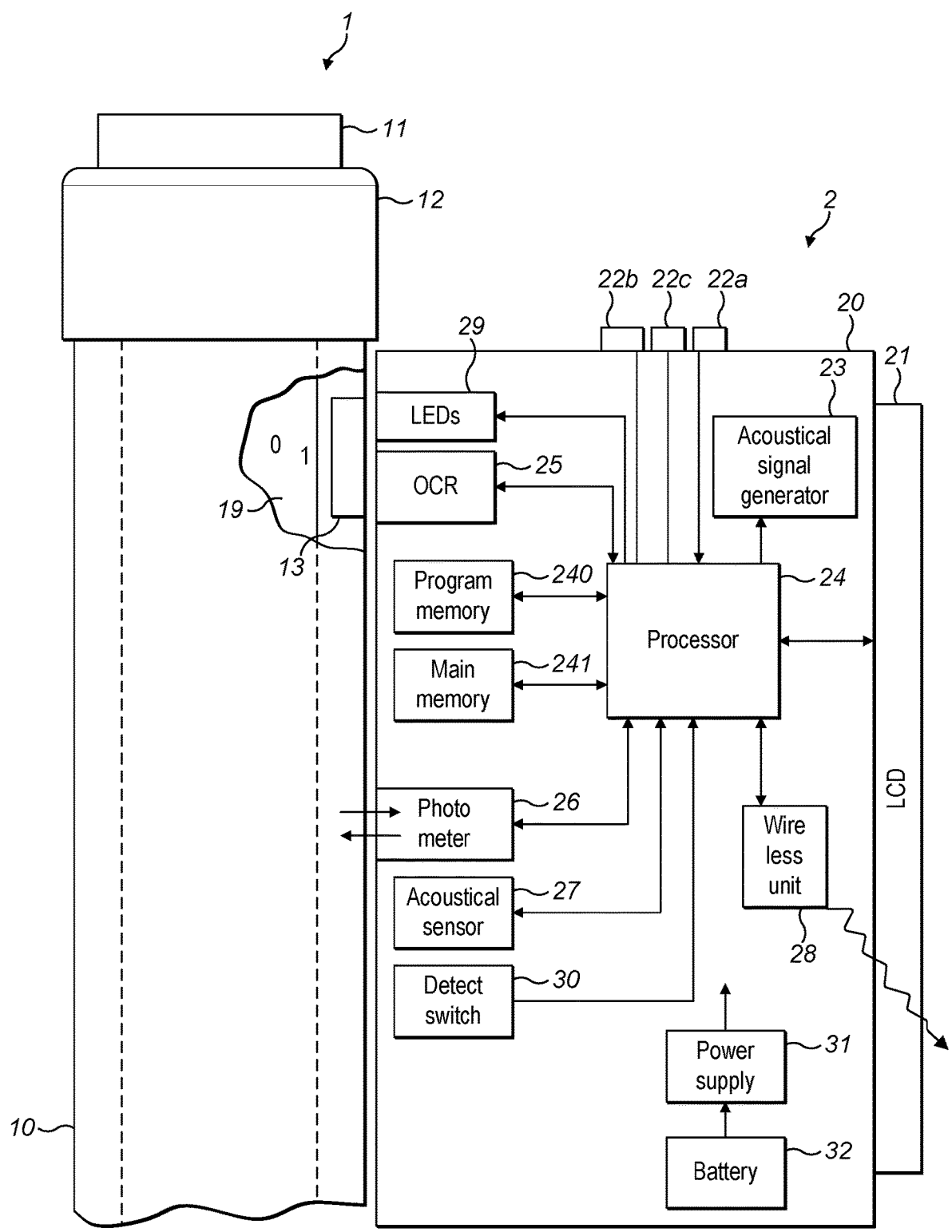
FIG. 6 is an internal schematic view of the supplemental device 2 in FIG. 4 or in FIG. 5 coupled to an injection device 1.

When coupled to an injection device 1, the supplemental device 2 may be caused to obstruct the dosage window 13 (as in FIG. 6). A supplemental device 2 configured to be used in this way contains one or more sensors, for example optical and/or acoustical sensors 25, 27 which gather information from the injection device 1. In particular the optical sensor(s) 25 gather information which is displayed in the dosage window 13. Such gathered information may then subsequently be displayed by display unit 21 provided on the supplemental device 2.

Figure 4:
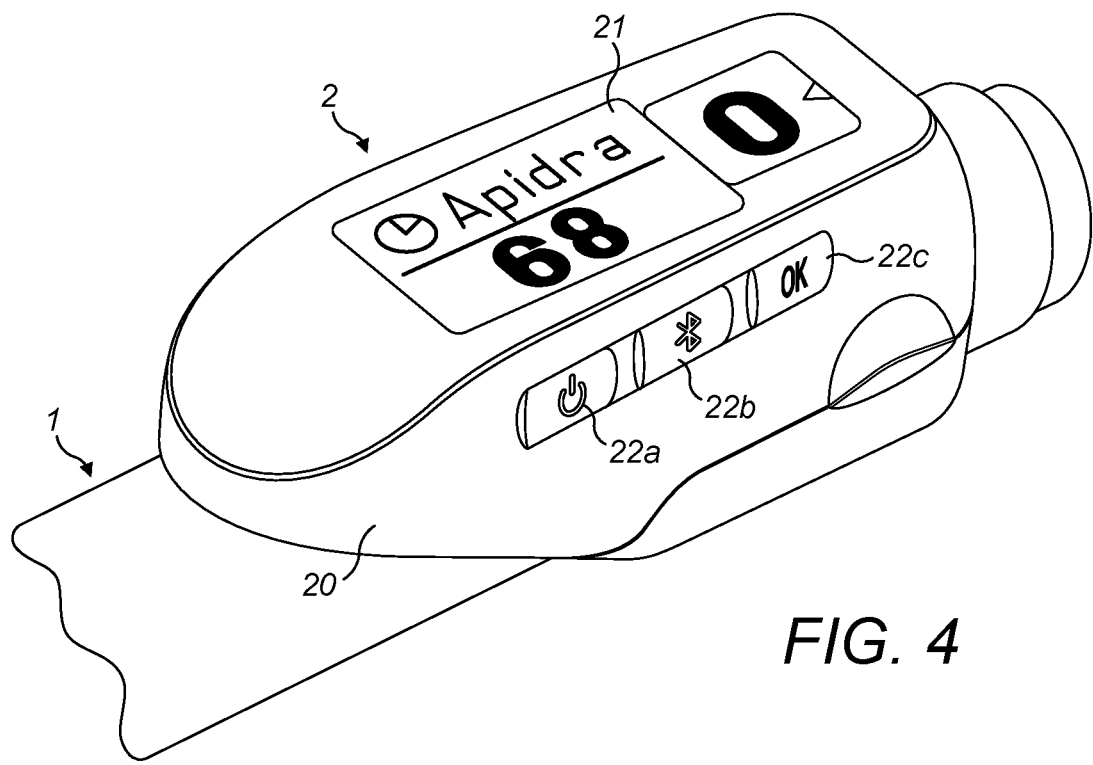
FIG. 4 is a perspective view of one embodiment of a supplemental device 2.

The supplemental device 2 further comprises one or more transducers for receiving user input, illustrated schematically as a single button 22 in FIG. 3 although a plurality of buttons may be provided instead as shown in FIGS. 4 and 6. Such input transducers may by used, inter alia, to turn on/off the supplemental device 2, trigger actions (which may involve causing the supplemental device 2 to pair or establish a connection with another device, and/or causing the device 2 to transmit information to another device), or to confirm something.

FIG. 4 depicts a perspective view of a supplemental device 2 according to one envisaged embodiment. The device 2 is coupled to an injection device 1 via a mating unit (not shown). As illustrated, information determined by the device 2 may be displayed using display unit 21. It will be appreciated that the dosage window 13 of the illustrated injection device 1 is obstructed by the supplemental device 2.

The embodiment depicted in FIG. 4 has three user input buttons (or switches). A first such button 22a is a power on/off button, actuation of which may cause the supplemental device 2 to be turned on and/or off. A second button 22b is a communications button actuation of which may cause the supplemental device 2 to pair or establish a connection with another device such as a computer (using Bluetooth for example). A third button 22c is a confirm or OK button actuation of which may be used to indicate a user's desired selection. The buttons 22a, 22b, 22c may be any suitable form of mechanical switch, electrical transducer switch, or electromechanical switch.

Figure 5:
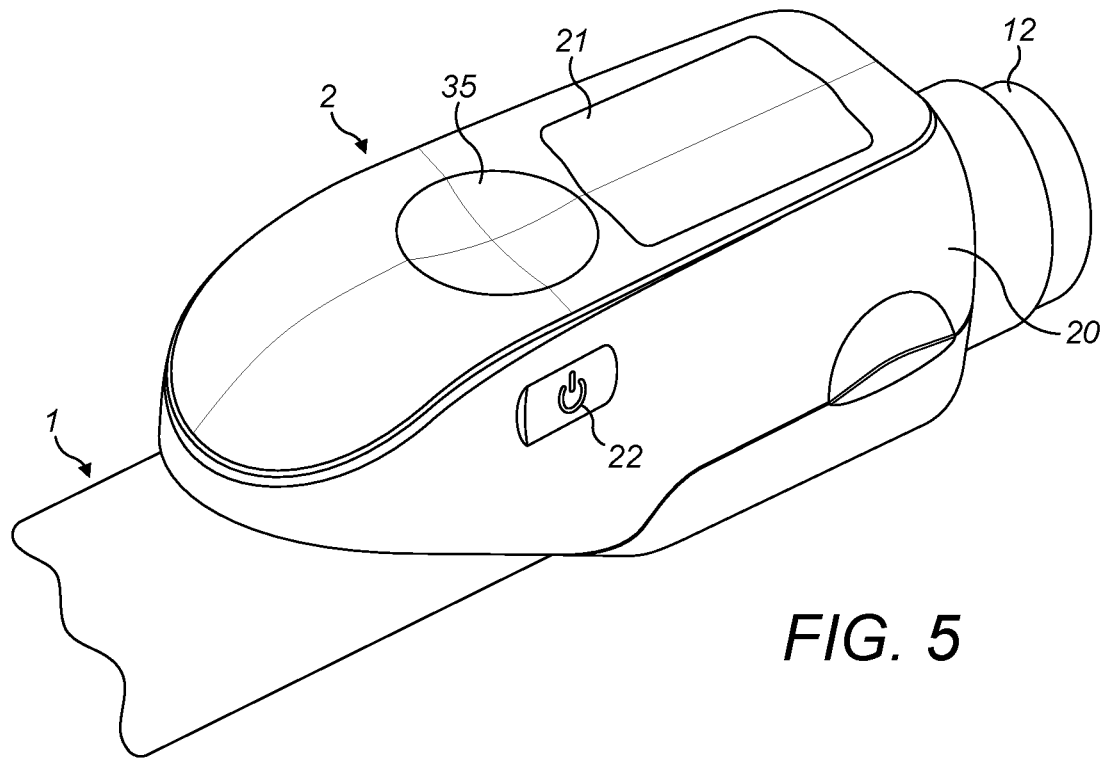
FIG. 5 is a perspective view of another embodiment of a supplemental device 2.

FIG. 5 depicts a perspective view of a supplemental device 2 according to another embodiment. The device is coupled to an injection device 1 via a mating unit (not shown). Information determined by the device 2 may be displayed using display unit 21. It will be appreciated that the dosage window 13 of the illustrated injection device 1 is obstructed by the supplemental device 2.

The embodiment depicted in FIG. 5 has a touch-sensitive transducer 35 for receiving user input. The device 2 is also provided with a single user input button (or switch 22). Actuation of the button 22 may cause the supplemental device 2 to be turned on and/or off. Manipulation of the touch sensitive input transducer 35 may trigger other actions involving, inter alia, causing the device 2 to pair or establish a connection with another device, triggering transmission of information from the supplemental device 2 to another device, and/or confirming something such as a user's desired selection.

FIG. 6 illustrates an internal schematic view of a supplemental device 2 of the kind depicted in FIG. 4 in a state where it is coupled to an injection device 1.

Within the housing 20 of the supplemental device 2, a variety of components are located. These are controlled by a processor 24 which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be non-volatile memory, such as Read-Only Memory (ROM), and main memory may for instance be a volatile memory, such as Random Access Memory (RAM). A logbook on performed ejections/injections may alternatively be stored in a flash memory coupled to the processor 24.

Upon actuation of the aforementioned first button 22*a* the processor may be sent a signal indicting that the supplemental device 2 is to be turned on and/or off. Actuation of the second button 22*b* (the communications button) may cause a signal to be sent to the processor, initiating the processor 24 to establish a connection between the supplemental device 2 and another device, or to trigger transmission of information from the supplemental device 2 to another device. A third button 22*c* is a confirm or OK button upon actuation of which the processor 24 may be sent a signal indicting a user's desired selection or confirmation. The third button 22*c* may be used to acknowledge information presented to a user of supplemental device 2, for example on the display unit 21.

In other embodiments such as the one depicted in FIG. 5, two of the buttons 22*b*, 22*c* may be omitted. Instead one or more capacitive sensors or other touch sensors may be provided.

Processor 24 is configured to control a display unit 21, which may be a Liquid Crystal Display (LCD) for example. The display unit 21 may be used to display information to a user of supplemental device 2. Examples of such information may include the present settings of the injection device 1, or information concerning a next injection to be given for instance the time remaining until when a next injection should be administered. The display unit 21 may be a touch-screen display for receiving user input and transferring it to the processor 24. The touch-sensitive transducer 35 in FIG. 5 may be part of such a touch-screen display.

The supplemental device 2 may be provided with an optical sensor 25 for reading information provided on the sleeve 19 through the dosage window 13. Such information may comprise numbers or other markings located on the sleeve 19 which indicate an amount of dose which has been dialled or is yet to be dispensed. The optical sensor 25 may be an Optical Character Recognition (OCR) reader that is capable of capturing images of the dosage window 13 in which a currently selected dose is displayed. The OCR reader 25 is further capable of recognizing characters (e.g. numbers) from the captured image and providing this information to processor 24.

Alternatively, the optical sensor 25 may be configured to merely capture images and provide information corresponding to such images to the processor 24. In such an arrangement the optical sensor 25 may be a camera and the processor 24 may be configured to perform the aforementioned OCR on the captured images.

The processor 24 constitutes a processor arrangement. The above mentioned OCR reader 25 may constitute a dose dialled detector operable to detect a dose of medicament dialled. The OCR reader 25 may also constitute a dose delivery determiner for determining that a dose of medicament has been delivered. The OCR reader 25 and the processor 24 may together constitute a quantity determiner for determining a quantity of medicament that has been delivered (and/or is yet to be dispensed, if any). The processor 24 provides a function of a clock configured to determine a current time.

A battery 32 powers the processor 24 and any other components comprising part of the supplemental device 2 by way of a power supply 31. Such other components will now be described. It will be appreciated that not all such other components are essential and a person skilled in the art may choose to omit one or more such components from a supplemental device. For example a supplemental device 2 may be made without the photometer 26 and/or pen detection switch 30 (both of which are described below).

The supplemental device 2 may be provided with a light-source, for example one or more light emitting diodes (LEDs) 29, to illuminate the dosage window 13 in which a currently selected dose is displayed. The processor 24 may be configured to control operation of such a light source. Furthermore, a diffuser may be provided in front of the light-source(s), for instance a diffuser made from a piece of acrylic glass. Additionally, the optical sensor 25 may comprise a lens (e.g. an aspheric lens) leading to a magnification (e.g. a magnification of more than 3:1).

The supplemental device 2 may be provided with a photometer 26 for determining an optical property of the housing 10 of injection device 1, for example a colour or a shading. The processor 24 may be configured to receive a signal from the photometer 26, thereby enabling the processor 24 to determine the particulars of said optical property. The optical property may be present in a specific portion of the housing 10. For example a colour or colour coding may be provided on the sleeve 19 or an insulin container comprised within the injection device 1. Also, the colour or colour coding may be visible through a further window in the housing 10 (and/or in the sleeve 19). Information relating to this colour may be provided to the processor 24 for determining the type of injection device 1 or the type of insulin contained within the injection device (e.g. SoloStar® Lantus® with purple colour and SoloStar® Apidra® with blue colour).

The supplemental device 2 may be provided with an acoustical sensor 27 for detecting sounds produced by an injection device 1. Such an acoustical sensor 27 may be used instead of or in conjunction with the optical sensor 25 heretofore described. The processor 24 may be configured to control and/or receive signals from such an acoustical sensor 27. Sounds may for instance occur when a dose is dialled by turning the dosage knob 12 and/or when a dose is ejected/injected by pressing injection button 11, and/or when a prime shot is performed. These actions are mechanically similar but nevertheless sound different when they are respectively performed (this may also be the case for electronic sounds, produced by acoustical signal generator 23 for instance, which indicate the occurrence of these actions). The acoustical sensor 27 and/or the processor 24 may be configured to differentiate between these different sounds in order to safely recognize that an injection has taken place (rather than merely a prime shot having been made).

The supplemental device 2 may be provided with a wireless unit 28 which the processor 24 may control in order to transmit information to, and/or receive information from, another device in a wireless fashion. Such transmission/reception may be based on radio transmission or optical transmission for example. In particular the wireless unit 28 may be a Bluetooth transceiver. Alternatively, the wireless unit 28 may be substituted or complemented by a wired unit which is configured to transmit information to, and/or receive information from, another device in a wire-bound fashion (such as via a cable or fibre connection). When data is transmitted, the units of the data (values) transferred may be explicitly or implicitly defined. For instance, in case of an insulin dose, always International Units (IU) may be used, or otherwise, the used unit may be transferred explicitly, for instance in coded form.

Lastly, the supplemental device 2 may be provided with a pen detection switch 30. Such a switch 30 may be operable to detect whether the pen 1 is present (i.e. to detect whether the supplemental device 2 is coupled to an injection device 1). When a pen 1 is detected (i.e. the supplemental device 2 is detected as being coupled to an injection device 1), the pen detection switch 30 may output a signal to the processor 24.

Figures 7, 8:
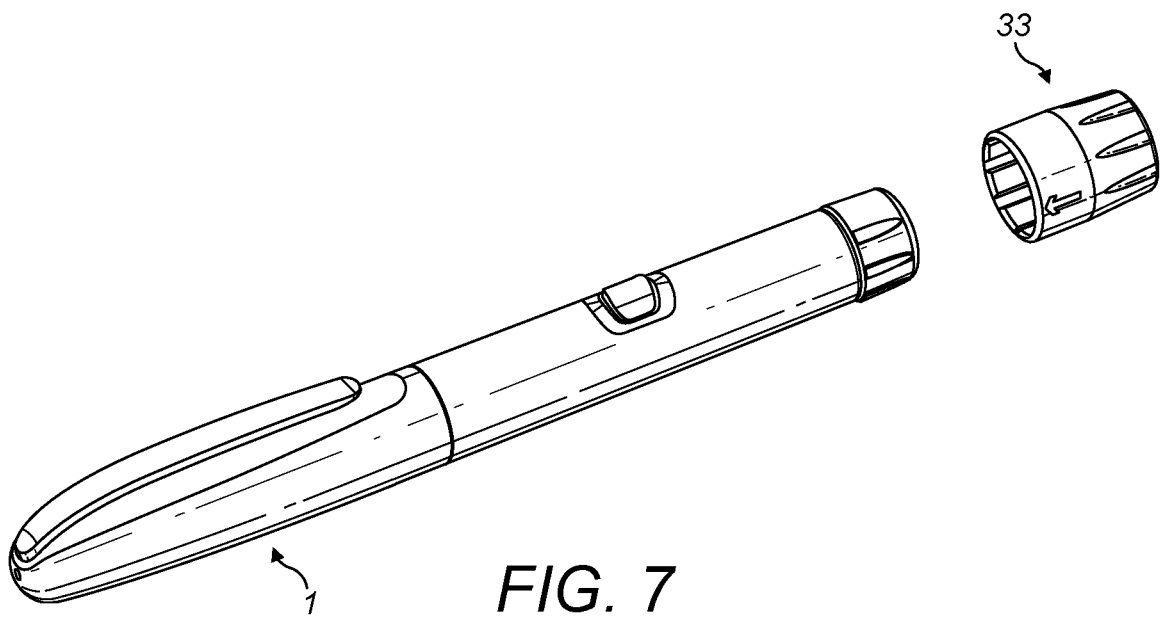
FIG. 7 is a perspective view of a further supplemental device being coupled to an injection device 1.
FIG. 8 illustrates an image which depicts dose information, as generated by a supplemental device of any of FIGS. 4, 5 and 7.

The supplemental device 2 depicted in FIG. 4 is capable of determining information related to a condition and/or use of the injection device 1. Such information may comprise information that human operators (users and/or medical practitioners) would be interested to be included in the aforementioned logbook on performed ejections/injections. Other supplemental devices 2 however may not be provided with a display unit 21 and may be configured to store information related to a condition and/or use of the injection device 1 without causing it to be displayed. An example of one such supplemental device 2 is illustrated in FIG. 7 in the form of an electronic module 33 that is capable of being fitted to the rear of an injection device 1.

In view of the foregoing it will be appreciated that supplemental devices 2 may be provided with one or different types of sensors for determining information relating to a condition and/or use of an injection device 1. It will further be appreciated that the supplemental devices 2 may be configured to cause such determined information to be saved in a storage space (for example main memory 241 or a removable memory card). In particular this information may comprise entries made in a logbook containing details of a dose history for a particular user.

Aspects of the invention described hereafter are not limited to the supplemental devices 2 depicted in the drawings but apply equally to supplemental devices for use with any kind of injection device, and supplemental devices provided with any combination of sensors for detecting information related to one or more conditions and/or use of an injection device.

A supplemental device 2 may be provided with sensors which enable the processor 24 of such device to determine: i) the size of an insulin dose delivered by an injection device; ii) the date and/or time when such dose was delivered; and/or iii) the latest BGM (blood glucose measurement) reading of the user's blood. Information relating to these parameters may be saved in a storage space located on the supplemental device (such as main memory 241 or a removable memory card) along with similar information determined at later or earlier times. This information collectively provides a dose history of the person using the injection device to which the supplemental device is coupled.

Information concerning each separate dose may be saved in the above mentioned storage space in a format that is only readable by propriety software. Such proprietary software may be utilised by the supplemental device, or a remotely located computer, to display and/or analyse dose history information. Additionally however (or instead) information concerning each separate dose may be saved in the storage space in an image format. Such an image format may be of either the lossy or lossless variety. Particular examples of image formats that may be used include, inter alia, raster format, vector format, compound format and stereo format. The processor may achieve conversion into an image format by taking the raw information relating to a dose, applying it to a template, and converting the completed template into an image file. More specifically information concerning each separate dose may be saved in the storage space in .JPEG format or .BMP format.

Saving information concerning each separate dose in .JPEG format (Joint Photographic Experts Group format) is advantageous because the .JPEG format is readable by a large array of commonly available electronic devices. This is particularly useful if the supplemental device is not itself capable of displaying dose history information (or is only capable of displaying some but not all dose history information), thereby requiring this information to be displayed on an additional electronic device such as a computer. FIG. 8 illustrates an example of a .JPEG image depicting dose information.

A person skilled in the art will appreciate that there are many ways in which dose history information stored in an image format may be transferred to another electronic device that is capable of displaying images. For example, the supplemental device may have a wireless unit 28 of the kind described in connection with FIG. 6. Such a wireless unit 28 may be used to wirelessly transfer data relating to images, which depict dose information, to a remote device. Alternatively the supplemental device may transfer data relating to images, which depict dose information, to a remote device via a cable or fibre connection. Such devices may be coupled via a USB interface for example. Furthermore, the storage space on which images that depict dose information are saved may be removable and connected to a remote device which is capable of displaying images. Such a removable storage space may for example comprise an SD card, an XD card or a USB memory stick, and may co-operate with (or be received in) a complementary interface provided on the supplemental device.

A removable storage space may serve as a secondary storage device in addition to a primary (or main) storage device that cannot be removed from a supplemental device. Information may be copied between such primary and secondary storage devices. A supplemental device may have one or more user interface features which upon manipulation cause a processor to copy information between the primary (non-removable) and secondary (removable) storage devices. For example, if a supplemental device is provided with a display unit 21, a menu feature may be displayed asking the user to indicate whether or not they want to copy information from the primary storage device to the secondary storage device or vice versa. Such a menu feature may be caused to be displayed upon connection of a secondary storage device to the supplemental device. A user may indicate a positive or negative selection via a short and/or long press of a particular combination of one or more transducers for receiving user input such as a button 22 or a touch-sensitive pad or transducer 35. In the case of supplemental devices that are not provided with a display unit 21 (and even those which are) a user may indicate whether or not they want to copy information between the primary and secondary storage devices at any particular time via a short and/or long press of a particular combination of one or more transducers for receiving user input (as before such transducers may comprise a button 22 or a touch-sensitive pad or transducer 35).

Figure 9:
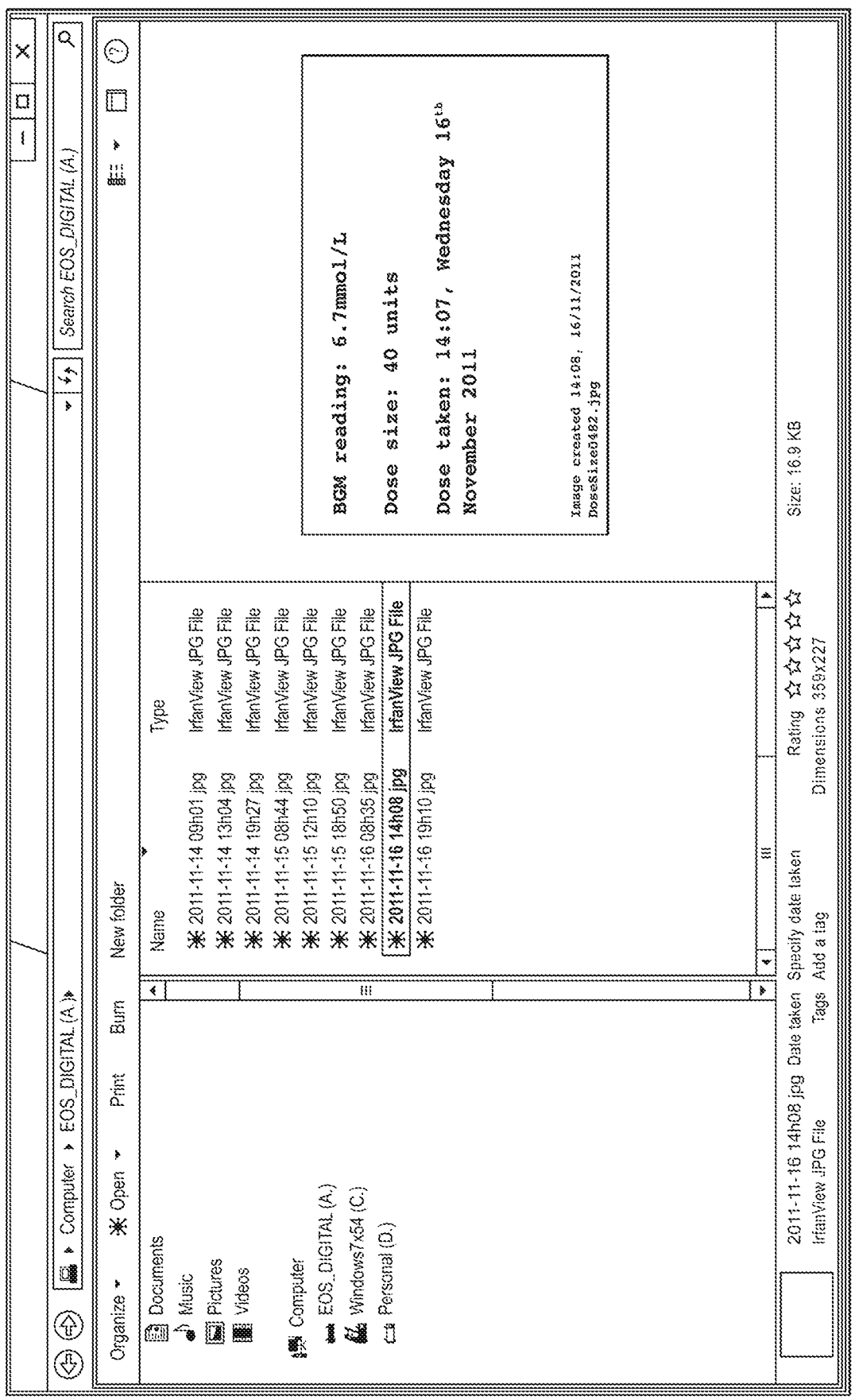
FIG. 9 illustrates a selection of dose information image files displayed on a computer.

If images that depict dose information are stored on a memory card, such images may be displayed on any device that is capable of reading that memory card to view files stored thereon. Some particular examples of devices that are capable of reading memory cards include digital cameras, computers, mobile phones, TVs and electronic photo frames. Advantageously, if a memory card is inserted into such an electronic device the files containing images, which depict dose information, will be automatically displayed in date and time order. This enables information concerning a particular dose to be quickly and easily located. FIG. 9 illustrates a plurality of such image files being displayed in date and time order on a computer.

According to another aspect of the invention, the functionality of a supplemental device that is capable of storing dose information in image format may be implemented by an injection device. For instance, features which correspond with those of a supplemental device heretofore described may be integral parts of an injection device. In one particular example, features corresponding with those of a supplemental device which has an acoustical sensor 27 in place of an optical sensor 25 may be integral parts of an injection device. Such injection devices are capable of storing dose information in image format (for instance .JPEG format) in the manner previously described. It should be noted that an injection device capable of storing dose information in image format may be provided with any combination of sensors for detecting information related to one or more conditions and/or use of the injection device.

It will be appreciated that the above described embodiments are purely illustrative and are not limiting on the scope of the invention. Other variations and modifications will be apparent to persons skilled in the art upon reading the present application. For instance any kind of information may be displayed in an image depicting information relevant to a particular dose. In particular, further to information picked up from the device sensor(s) other information which was relevant at the time when a particular dose is administered may be included in the image. Additional examples of information that may be included in an image depicting dose information (such as the one in FIG. 8) may include a patient's name to whom a dose was administered and/or other details of that patient, a medical practitioner's name responsible for the patient using the injection device used, the type of insulin (or other medicament) delivered, the type of injection device used, a recommended amount of dose to be administered and an actual amount of dose that was delivered.

Finally, it be appreciated that the functionality described herein which relates to the storage of information, detected by one or more sensors, in an image format applies to injection devices configured to inject any kind of medicament and not solely those used for injecting insulin. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A supplemental device configured to determine information related to an injection device, the supplemental device being configured to be coupled to the injection device, wherein the supplemental device comprises:
   a detector configured to detect an optical property of a portion of the injection device and output a signal associated with the optical property;
   a processor configured to receive the signal associated with the optical property from the detector;
   a memory configured to store information associated with the optical property; and
   a wireless unit configured to transmit the information associated with the optical property to another device.

2. The supplemental device of claim 1, further comprising one or more light emitting diodes (LEDs).

3. The supplemental device of claim 1, further comprising a dose dialed detector operable to detect a dose of medicament dialed at the injection device.

4. The supplemental device of claim 1, further comprising a dose delivery determination unit configured to determine that a dose of medicament is delivered.

5. The supplemental device of claim 1, wherein the supplemental device further comprises sensors configured to enable the processor to determine a size of a medicament dose delivered by the injection device.

6. The supplemental device of claim 5, wherein the processor is configured to determine a date and/or time when the medicament dose is delivered.

7. The supplemental device of claim 1, wherein the optical property is a color.

8. The supplemental device of claim 7, wherein the processor is configured to determine a type of the injection device based on the color.

9. The supplemental device of claim 7, wherein the processor is configured to determine a type of insulin contained within the injection device based on the color.

10. The supplemental device of claim 1, further comprising a switch operable to detect whether the supplemental device is coupled to the injection device.

11. The supplemental device of claim 10, wherein the signal output by the detector to the processor is a first signal, and
   the switch is configured to output a second signal to the processor.

12. The supplemental device of claim 1, wherein the wireless unit comprises a Bluetooth transceiver.

13. The supplemental device of claim 1, wherein the injection device is an injection pen.

14. A system comprising:
   an injection device, and
   a supplemental device configured to determine information related to the injection device, the supplemental device being configured to be coupled to the injection device, wherein the supplemental device comprises:

a detector configured to detect an optical property of a portion of the injection device and output a signal associated with the optical property;

a processor configured to receive the signal associated with the optical property from the detector;

a memory configured to store information associated with the optical property; and a wireless unit configured to transmit the information associated with the optical property to another device.

15. The system of claim 14, wherein the supplemental device further comprises one or more light emitting diodes (LEDs).

16. The system of claim 14, wherein the supplemental device further comprises a dose dialed detector operable to detect a dose of medicament dialed at the injection device.

17. The system of claim 14, wherein the supplemental device further comprises a dose delivery determination unit configured to determine that a dose of medicament is delivered.

18. The system of claim 14, wherein the supplemental device further comprises sensors configured to enable the processor to determine a size of a medicament dose delivered by the injection device.

19. The system of claim 18, wherein the processor is configured to determine a date and/or time when the medicament dose is delivered.

20. The system of claim 14, wherein the optical property is a color.

* * * * *